ns of α-AMINO ACIDS

[75] Inventors: Brian W. Metcalf, Strasbourg; Michel Jung, Illkirch Graffenstaden, both of France

[73] Assignee: Merrell Toraude et Compagnie, Strasbourg, France

[21] Appl. No.: 812,067

[22] Filed: Jul. 1, 1977

[51] Int. Cl.² ............... C07D 211/72; C07D 223/10; C07C 101/24
[52] U.S. Cl. ........................ 546/243; 260/239 B; 260/558 A; 260/558 S; 260/559 A; 260/559 T; 260/561 A; 424/253; 424/300; 424/311; 424/319; 424/320; 536/26; 560/16; 560/25; 560/39; 560/41; 560/153; 560/158; 560/168; 560/169; 562/426; 562/448; 562/450; 562/556; 562/560; 562/561
[58] Field of Search ............... 562/561, 556, 560, 426, 562/450, 448; 560/168, 158, 41, 39, 169, 25, 16, 153; 536/26; 260/561 A, 558 A, 559 A, 559 T, 558 S, 239 B; 546/243

[56] References Cited

U.S. PATENT DOCUMENTS

| 2,513,831 | 7/1950 | Warner et al. | 546/243 |
| 3,959,356 | 5/1976 | Metcalf et al. | 562/561 X |
| 4,133,964 | 1/1979 | Metcalf et al. | 562/561 X |
| 4,139,563 | 2/1979 | Metcalf et al. | 260/583 H |

*Primary Examiner*—John M. Ford
*Assistant Examiner*—Richard A. Schwartz
*Attorney, Agent, or Firm*—L. Ruth Hattan; Eugene O. Retter; George W. Rauchfuss, Jr.

[57] ABSTRACT

Novel acetylenic derivatives of α-amino acids of the following general structure:

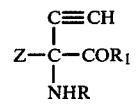

wherein Z is β-methylthioethyl, β-benzylthioethyl, S-(5'-desoxyadenosin-5'-yl)-S-methylthioethyl, γ-guanidinopropyl, or $RHN(CH_2)_n$—; n is the integer 3 or 4; each R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

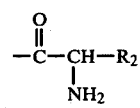

wherein $R_2$ is hydrogen, a straight or branched lower alkyl group of from 1 to 4 carbon atoms, benzyl or p-hydroxybenzyl; $R_1$ is hydroxy, a straight or branched alkoxy group of from 1 to 8 carbon atoms, $-NR_4R_5$ wherein each of $R_4$ and $R_5$ is hydrogen or a lower alkyl group of from 1 to 4 carbon atoms, or

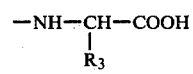

wherein $R_3$ is hydrogen, a straight or branched lower alkyl group of from 1 to 4 carbon atoms, benzyl or p-hydroxybenzyl; and the lactams thereof when Z is $RHN(CH_2)_n$— and each R is hydrogen; with the provisos that when Z is β-benzylthioethyl or S-(5'-desoxyadenosin-5'-yl)-S-methyl-thioethyl, R is hydrogen and $R_1$ is hydroxy, when Z is γ-guanidinopropyl, R is hydrogen and $R_1$ is hydroxy or a straight or branched lower alkoxy group of from 1 to 8 carbon atoms, and when Z is $RHN(CH_2)_n$— both R groups are the same; and pharmaceutically acceptable salts and individual optical isomers thereof.

8 Claims, No Drawings

α-ACETYLENIC DERIVATIVES OF α-AMINO ACIDS

FIELD OF INVENTION

This invention relates to novel pharmaceutically useful acetylenic derivatives of α-amino acids.

SUMMARY OF INVENTION

The compounds of the present invention may be represented by the following general Formula 1:

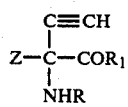

Formula I

In the above general Formula 1 Z is β-methylthioethyl, β-benzylthioethyl, S-(5'-desoxyadenos in-5'-yl)-β-methyl-thioethyl, γ-guanidinopropyl, or $RHN(CH_2)_n-$; n is the integer 3 or 4; each R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or the group

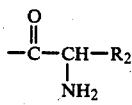

wherein $R_2$ is hydrogen, a straight or branched lower alkyl group of from 1 to 4 carbon atoms, benzyl or p-hydroxybenzyl; and $R_1$ is hydroxy, a straight or branched alkoxy group of from 1 to 8 carbon atoms, $-NR_4R_5$ wherein each $R_4$ and $R_5$ is hydrogen or a lower alkyl group of from 1 to 4 carbon atoms, or the group

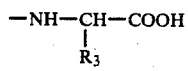

wherein $R_3$ is hydrogen, a straight or branched lower alkyl group of from 1 to 4 carbon atoms, benzyl or p-hydroxybenzyl; with the provisos that when Z is β-benzylthioethyl or S-(5'-desoxyadenos in-5'-yl)-S-methylthioethyl, R is hydrogen and $R_1$ is hydroxy, when Z is γ-quanidinopropyl, R is hydrogen and $R_1$ is hydroxy or a straight or branched lower alkoxy group of from 1 to 8 carbon atoms, and when Z is RHN $(CH_2)_n-$ both R groups are the same. The lactams of the compounds of general Formula I wherein Z is $RHN(CH_2)_n-$ and each R is hydrogen are also within the scope of the present invention. Pharmaceutically acceptable salts and individual optical isomers of the compounds of general Formula I are also included within the scope of the present invention.

DETAILED DESCRIPTION OF INVENTION

In the above general Formula I in addition to the group $RHN(CH_2)_n-$, the symbol Z represents the substituent groups β-methylthioethyl, β-benzylthioethyl, S-(5'-desoxyadenosin-5'-yl)-β-methylthioethyl and γ-guanidinopropyl which are depicted by the following structures:

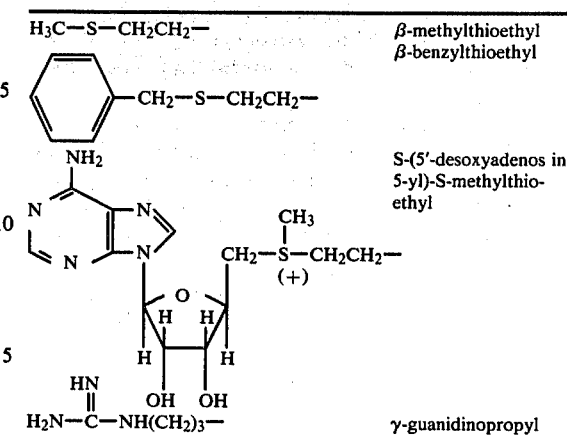

As used in general Formula I the term alkylcarbonyl is taken to mean the group

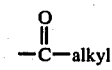

wherein the alkyl moiety has from 1 to 4 carbon atoms and is straight or branched, for example, methyl, ethyl, n-propyl, isopropyl, n-butyl, isobutyl and tert-butyl.

As used in general Formula I the term alkoxycarbonyl is taken to mean the group

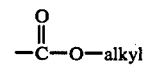

wherein the alkoxy moiety, that is, —O-alkyl, has from 1 to 4 carbon atoms and is straight or branched, for example, methoxy, ethoxy, n-propoxy, isopropoxy, n-butoxy, and tert-butoxy.

Illustrative examples of straight or branched alkyl groups having from 1 to 4 carbon atoms as used in general Formula I are methyl, ethyl, n-propyl, n-butyl, isopropyl and tert-butyl.

Illustrative examples of alkoxy groups having from 1 to 8 carbon atoms as used in general Formula I are methoxy, ethoxy, isopropoxy, tert-butoxy, pentyloxy, and octyloxy.

The lactams of the compounds of general Formula I wherein Z is $RHN(CH_2)_n-$, and each R is hydrogen are represented by the following general Formula II:

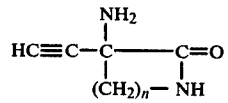

Formula II

In the above general Formula II, n is the integer 3 or 4.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, malonic, tartaric, citric, cyclamic and ascorbic acids; and non-toxic salts formed with inorganic or organic bases such as those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine and piperazine. The salts are prepared by conventional means.

Preferred compounds of this invention are those of general Formula I wherein $R_1$ is hydroxy. More preferred compounds of this invention are those of general Formula I wherein $R_1$ is hydroxy, Z is β-methylthioethyl, S-(5'-desoxyadenos in -5'-yl)-S-methylthioethyl, γ-guanidinopropyl or $RHN(CH_2)_n$—and each R is hydrogen and the lactams of said compounds wherein Z is $RHN(CH_2)_n$—as represented by the following general Formula III:

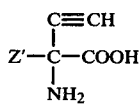

Formula III

In the above general Formula III Z' is β-methylthioethyl, S-(5'-desoxyadenos in-5'-yl)-S-methylthioethyl, γ-guanidinopropyl or $H_2N(CH_2)_n$—wherein n is the integer 3 or 4. The lactams of the compounds of general Formula III wherein Z is $H_2N(CH_2)_n$—are represented hereinabove by general Formula II.

Illustrative examples of compounds of the present invention are the following:
αacetylene-α-amino-γ-methylthiobutyric acid,
α-acetylene-α-amino-γ-benzylthiobutyric acid,
α-acetylene-α-amino-γ-[S-(5'-desoxyadenos in-5'-yl)-S-(methyl)thio]butyric acid,
α-acetylene-α-amino-δ-guanidinovaleric acid,
α-acetylene-α,δ-diaminovaleric acid,
α-acetylene-α,ε-diaminocaproic acid,
methyl α-acetylene-α-amino-γ-methylthiobutyrate,
methyl α-acetylene-α-amino-δ-guanidinovalerate,
methyl α-acetylene-α,δ-diaminovalerate,
methyl α-acetylene-α,ε-diaminocaproate,
ethyl α-acetylene-α-amino-γ-methylthiobutyrate,
ethyl α-acetylene-α-amino-δ-guanidinovalerate,
ethyl α-acetylene,α,δ-diaminovalerate,
ethyl α-acetylene-α,ε-diaminocaproate,
n-propyl α-acetylene-α-amino-γ-methylthiobutyrate,
n-propyl α-acetylene-α-amino-δ-guanidinovalerate,
n-propyl α-acetylene-α,δ-diaminovalerate,
n-propyl α-acetylene-α,ε-diaminocaproate,
n-butyl α-acetylene-α-amino-γ-methylthiobutyrate,
n-butyl α-acetylene-α-amino-δ-guanidinovalerate,
n-butyl α-acetylene-α,δ-diaminovalerate,
n-butyl α-acetylene-α,ε-diaminocaproate,
isopropyl α-acetylene-α-amino-γ-methylthiobutyrate,
tert-butyl α-acetylene-α-amino-δ-guanidinovalerate,
hexyl α-acetylene-α,δ-diaminovalerate,
heptyl α-acetylene-60 ,ε-diaminocaproate,
octyl α-acetylene-α-amino-γ-methylthiobutyrate,
pentyl α-acetylene-α-amino-δ-guanidinovalerate,
N,N-dimethyl-α-acetylene-α,δ-diaminovaleramide,
isopropyl α-acetylene-α,δ-diaminovalerate,
pivalyl α-acetylene-α,ε-diaminocaproate,
N-methyl-α-acetylene-α-amino-γ-methylthiobutyramide,
N-n-butyl-α-acetylene-α,δ-diaminovaleramide,
N-ethyl-α-acetylene-α,ε-diaminocaproamide,
2-acetylene-2-amino-4-methylthio-1-oxobutylaminoacetic acid,
2-(2-acetylene-2-amino-1-oxo-1,5-pentylenediamine)-phenyl-propionic acid,
α-acetylene-α,ε-di-(1-oxopropylamino)caproic acid,
α-acetylene-γ-methylthio-α-(1-oxopropylamino)valeric acid,
α-acetylene-α,δ-di-(ethoxycarbonyl)valeric acid,
N-methyl-α-acetylene-α,δ-di-(1-oxoethylamino)valeramide, and methyl α-acetylene-α,ε-di-(2-amino-1-oxoethylamino)caproate.

The compounds of general Formula I have many utilities. The compound of general Formula I wherein Z is β-benzylthioethyl, R is hydrogen and $R_1$ is hydroxy is useful as an intermediate in the preparation of the corresponding pharmaceutically useful compound wherein Z is S-(5'-desoxyadenosin-5'-yl)-S-metylthioethyl.

The compounds of general Formulas I and II wherein Z is other than β-benzylthioethyl are irreversible inhibitors of decarboxylase enzymes which are involved in polyamine formation rendering said compounds useful as pharmacological agents. Polyamines, particularly putrescine, spermidine and spermine are present in plant and animal tissues and in some microorganisms. Although the exact physiological role of polyamines has not been clearly delineated there is evidence to suggest that polyamines are involved with cell division and growth. (H. G. Williams-Ashman et al., The Italian J. Biochem. 25, 5-32 (1976), A Raina and J. Janne, Med. Biol. 53, 121-147 (1975) and D. H. Russell, Life Sciences 13, 1635-1647 (1973)). Polyamines are essential growth factors for or involved in the growth processes of certain microorganisms, for example, *E. coli*, Enterobacter, Klebsiella, *Staphylcoccus aureus, C. Cadaveris*, Samonea typhosa and *Haemophilus parainfluenza*. Polyamines are associated with both normal and neoplastic rapid growth there being an increase in the synthesis and accumulation of polyamines following a stimulus causing cellular proliferation. Also, levels of polyamines are known to be high in embryonic systems, the testes, in patients with rapidly growing tumors, leukemic cells and other rapidly growing tissues. It is known that there is a correlation between the activity of the decarboxylase enzymes of ornithine, S-adenosylmethionine, arginine and lysine and polyamine formation.

The biosyntheses of putrescine, spermidine and spermine are interrelated Putrescine is the decarboxylation product of ornithine, catalyzed by ornithine decarboxylase. Putrescine formation may also occur by decarboxylation of arginine to form agmatine which is hydrolyzed to give putrescine and urea. Arginine is also involved in ornithine formation by action of the enzyme arginase. Activation of methionine by S-adenosylmethionine synthetase forms S-adenosylmethionine which is decarboxylated, afterwhich the propylamine moiety of activated methionine may be transferred to putrescine to form spermidine or the polyamine moiety may be transferred to spermidine to form spermine. Hence, putrescine serves as a precursor to spermidine and spermine and additionally has been shown to have a marked regulatory effect upon the polyamine biosynthetic pathway in that it has been shown that increased synthesis of putrescine is the first indication that a tissue will undergo renewed growth processes. Cadaverine which is the decarboxylation product of lysine has been shown to stimulate the activity of S-adenosylmethionine decarboxylase and is known to be essential to growth processes of many microorganisms, for example, *H. parainfluenza.*

The compounds of general Formula I wherein Z is RHN(CH₂)ₙ— and the lactams thereof are irreversible inhibitors of ornithine decarboxylase and lysine decarboxylase respectively as n varies from 3 to 4. The compounds of general Formula I wherein Z is β-methylthioethyl or S-(5'-desoxyadenosin-5'-yl)-β-methylthioethyl are irreversible inhibitors of S-adenosylmethionine decarboxylase and wherein Z is γ-guanidinopropyl are irreversible inhibitors of arginine decarboxylase. As irreversible inhibitors of the above-enumerated decarboxylase enzymes the compounds of general Formulas I and II wherein Z is other than β-benzylthioethyl are useful as antiinfective agents being effective in the control of microorganisms, for example, bacteria, fungi and viruses which are dependent upon polyamines for growth, for example, *E. coli,* Enterobacter, Klebsiella, *Staphylococcus aureus, C. Cadaveris,* viruses such as, *H. parainfluenza,* picornaviruses, for example, Encephalomyocarditis, *Herpes simplex,* poxviruses and arboviruses, for example, *Semliki forest.* The compounds of general Formulas I and II wherein Z is other than β-benzylthioethyl and RHN(CH₂)₄— are also useful in the control of certain rapid growth processes and said compounds may be used alone or in combination with one another. For example, the compounds are useful in the inhibition of spermatogenesis and embryogenesis and therefore the compounds find use as male antifertility agents and abortifacients. The compounds are also useful in the inhibition of the immune response, thus the compounds are useful as immunosuppressants for the treatment, for example, of myasthenia gravis, arthritis, multiple sclerosis and the prevention of tissue or organ transplant rejection and are useful in the control of neoplastic growth, for example, solid tumors, leukemias and lymphomas. The compounds are also so useful as inhibitors of prostatic hypertrophy, excessive scalp cell growth as found with the occurrence of dandruff and as inhibitors of abnormal cutaneous cell growth as found with a psoriatic condition.

The utility of compounds of general Formula I as irreversible inhibitors of ornithine or S-adenosylmethionine decarboxylases in vivo can be demonstrated as follows. An aqueous solution of an appropriate compound of Formula I is given orally or parenterally to male mice or rats. The animals are sacrificed 1 to 48 hours after administration of the compound, and the ventral lobes of the prostrate removed and homogenized with the activity of ornithine and S-adenosylmethionine decarboxylases being measured as generally described by E. A. Pegg and H. G. Williams-Ashman, Biochem. J. 108, 533–539 (1968) and J. Janne and H. G. Williams-Ashman, Biochem. and Biophys. Res. Comm. 42, 222–228 (1971).

The compounds of general Formula I wherein R₁ is hydroxy are useful as chemical intermediates for the preparation of novel cephalosporin derivatives which are useful as antibiotics and have the following general structure:

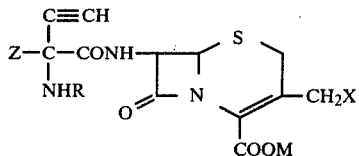

Formula V wherein Z and R have the meanings defined in general Formula I; M is hydrogen or a negative charge; and X is hydrogen or acetoxy.

The compounds of general Formula V and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula V and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula V, salts and isomers thereof may be incorporated into creams or ointments.

Illustrative examples of bacteria against which the compounds of general Formula V and the pharmaceutically acceptable salts and individual optical isomers thereof are active are *Staphyloccus aureus, Salmonella schotmuehleri, Klebsiella pneumoniae, Diplococcus pneumoniae* and *Streptococcus pyogenes.*

Illustrative pharmaceutically acceptable non-toxic inorganic acid addition salts of the compounds of general Formula V are mineral acid addition salts, for example, hydrogen chloride hydrogen bromide, sulfate, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of compounds of general Formula V are 7-[[2-acetylene-2,5-diaminovaleryl]amino]-3-acetyloxymethyl-8-oxo-5-thia-1-azabicyclo[4.2.0]-oct-2-ene-2-carboxylic acid, 7-[[2-acetylene-2,6-diaminocaproyl ]-3-acetyloxymethyl -8-oxo-5-thia-1azabicyclo[4.2.0]oct-2-ene-2-carboxylic acid and 7-[[2-acetylene-2-amino-δ-guanidinovaleryl]]amino]-3-acetyloxymethyl-8-oxo-5-thia-1-azabicyclo[4.2.0]oct-2-ene-2-carboxylic acid.

The preparation of the compounds of general Formula V is described hereinbelow.

As pharmacologically useful agents the compounds of general Formulas I and II wherein Z is other than βbenzylthioethyl can be administered in various manners to the patient being treated to achieve the desired effect. The compounds can be administered alone or in the form of a pharmaceutical preparation orally, parenterally, for example, intravenously, intraperitoneally, or subcutaneously, or topically. The amount of compound administered will vary over a wide range and can be any effective amount. Depending on the patient to be treated, the condition being treated and the mode of administration, the effective amount of compound administered will vary from about 0.1 mg/kg to 500 mg/kg of body weight of the patient per unit dose and preferably will be about 10 mg/kg to about 100 mg/kg of body weight of patient per unit dose. For example, a typical unit dosage form may be a tablet containing from 10 to 300 mg of a compound of Formulas I or II which may be administered to the patient being treated 1 to 4 times daily to achieve the desired effect.

As used herein the term patient is taken to mean warm blooded animals such as mammals, for example, cats, dogs, rats, mice, guinea pigs, horses, bovine cows, sheep and humans.

The solid unit dosage forms can be of the conventional type. Thus, the solid form can be a capsule which can be of the ordinary gelating type containing a novel compound off this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose, and related sugars solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds of general Formula I wherein X is $\beta$-methylthioethyl, $\beta$-benzylthioethyl, or $RHN(CH_2)_n-$, $R_1$ is hydroxy and each R is hydrogen are prepared by treating a suitably protected propargylamine derivative with a strong base to form a protected propargylamine carbanion intermediate which is reacted with an lkylating reagent of the formula $R_6X$ wherein X is halogen, for example, chlorine or bromine, and $R_6$ is $\beta$-methylthioethyl, $\beta$-benzylthioethyl or $PhHC=N(CH_2)_n-$ wherein n is the integer 3 to 4, treating the thus formed alkylated protected propargylamine derivative with a strong base to form an alkylated protected propargylamine carbanion, reacting said second carbanion with an acylating reagent and subsequently removing the protecting groups by acid or base hydrolysis as represented by the following reaction scheme:

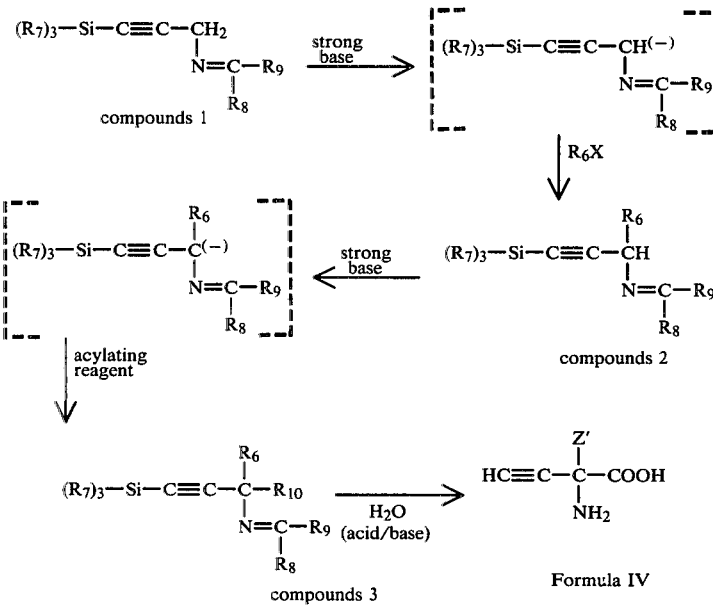

In the above reaction scheme $R_6$ and X have the meanings defined hereinabove; Ph represents phenyl; $R_8$ is hydrogen, methoxy or ethoxy; $R_9$ is phenyl, tert-butyl, or triethylmethyl; $R_7$ is a straight or branched lower alkyl group having from 1 to 4 carbon atoms, such as, methyl, ethyl, n-propyl and tert-butyl; $R_{10}$ is a carboxy anion, a carboxylic acid ester, a carboxamide, a nitrile or other group capable of being hydrolyzed to a carboxylic acid function which varies with the acylating reagent employed; and Z' is $\beta$-methylthioethyl, $\beta$-benzylthioethyl or $H_2N(CH_2)_n-$ wherein n is the integer 3 or 4.

Suitable strong bases which may be employed in the above reaction to form each carbanion are those which will abstract a proton from the carbon atom adjacent to the acetylene moiety, such as, alkyl lithium, for example, butyl lithium or phenyl lithium, lithium di-alkylamide, for example, lithium diisopropylamide, lithium amide, ertiary potassium butylate or sodium amide.

The alkylating reagents, $R_6X$, employed in the above reaction are known in the art or can be prepared by methods known in the art. The reactant $PhHC=N(CH_2)_n$— can be prepared, for example, by reacting 3-bromo-n-propylamine hydrochloride or 4-bromo-n-butylamine hydrochloride with benzaldehyde in an organic amine, such as, triethylamine.

Suitable acylating reagents which may be employed in the above reaction are halo-formates, such as chloro methylformate or chloro ethylformate, azido tert-butylformate, cyanogen bromide, carbon dioxide, diethylcarbonate, phenylisocyanate, triethoxymethylium tetrafluoroborate, N,N-dimethylcarbamoyl chloride, 2-methylthio-1,3-dithiolinium iodide, ethylene carbonate or ethylene trithiocarbonate. When 2-methylthio-1,3-dithiolinium iodide is employed the additional step of alcoholysis with a lower alcohol, for example ethanol or isopropyl alcohol is required prior to deprotection by hydrolysis.

The alkylating reaction and the acylating reaction may be carried out in an aprotic solvent, for example, benzene, toluene, ether, tetrahydrofuran, dimethylsulfoxide, dimethylformamide, dimethyl acetamide, hexamethyl phosphortriamide. For each reaction the temperature varies from $-120°$ C. to about 25° C., a preferred reaction temperature being about $-70°$ C., and the reaction time varies from about 178 hour to 24 hours.

Removal of the protecting groups, as represented in the reaction scheme in the step going from compounds 3 to compounds of Formula IV, is achieved by treatment with aqueous acid, for example, hydrochloric acid or toluene sulfonic acid, or aqueous base, for example, sodium hydroxide or potassium hydroxide. Optionally hydrazine or phenylhydrazine may be employed in removing the protecting groups.

The propargylamine derivatives, that is, compounds 1, wherein $R_8$ is hydrogen are prepared by the addition of protecting groups on the acetylene function and the nitrogen function of propargylamine. Protection of the nitrogen function of the propargylamine is accomplished by forming in a known manner a Schiff's base with a nonenolizable carbonyl bearing compound selected from benzaldehyde, 2,2-dimethylpropanal and 2,2-diethylbutanal. Protection of the acetylenic function is accomplished by reacting the above-described Schiff's base with a trialkylsilyl chloride wherein the alkyl moiety has from 1 to 4 carbon atoms and is straight or branched, for example, trimethylsilylchloride or triethylsilylchloride forming in a known manner the corresponding trialkylsilyl derivative.

The propargylamine derivatives, compounds 1, wherein $R_8$ is methoxy or ethoxy are prepared by reacting propargylamine wherein the acetylene function is protected by a trialkylsilyl group, wherein the alkyl moiety has from 1 to 4 carbon atoms and is straight or branched, with benzoyl chloride, pivalic acid chloride, or 2,2-diethylbutyric acid chloride at 0° C. in diethyl ether, dioxane, tetrahydrofuran, chloroform, methylenechloride, dimethylformamide, dimethylacetamide, or chlorobenzene in the presence of an organic base as triethylamine or pyridine after which the reaction mixture is allowed to warm to about 25° C. for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_8$ is methoxy or triethyloxonium tetrafluoroborate when $R_8$ is ethoxy at about 25° C. in a chlorinated hydrocarbon solvent such as methylene chloride, chlorobenzene or chloroform, and the reaction mixture is refluxed for about 12 to 20 hours. The mixture is then cooled to about 25° C. and an organic base such as triethylamine or pyridine is added, after which the solution is extracted with brine and the product isolated.

The protected propargylamine starting material is obtained by treating a 3-trialkylsilylprop-2-ynyl-1-iminobenzyl derivative, that is compounds 1 wherein $R_8$ is hydrogen and $R_9$ is phenyl with hydrazine or phenylhydrazine at about 25° C. for about ½ hour after which the mixture is diluted with, for example, petroleum ether, benzene or toluene and the amine isolated. Alternatively the imine is hydrolyzed with 0.5 to 1 N HCl, and the aqueous phase evaporated to afford the amine hydrochloride.

The compounds of general Formula I wherein Z is γ-guanidinopropyl, $R_1$ is hydroxy and R is hydrogen are prepared from the corresponding derivative wherein Z is $RHN(CH_2)_n$—wherein R is hydrogen and n is the integer 3, that is, the compound

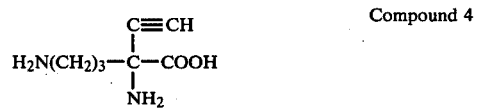

Compound 4 by treatment with an alkylisothiouronium salt, for example, ethylisothiouronium hydrobromide by procedures generally known in the art, for example, Organic Synthesis, III, p. 440 (1955). The reaction is carried out in the presence of a base, such as aqueous sodium hydroxide or potassium hydroxide at a pH of about 10 at a temperature of about 25° C. for about 2 to 6 hours after which the reaction mixture is neturalized with concentrated hydrochloric acid and the product isolated.

The compound of Formula I wherein Z is S-(5'-desoxyadenosin-5'-yl)-S-methylthioethyl, is prepared by treating for about one hour the corresponding compound wherein Z is β-benzylthioethyl, that is, the compound

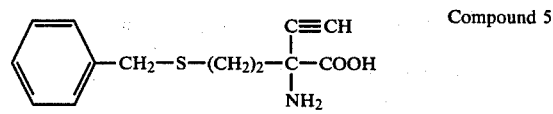

Compound 5 with sodium amide or lithium amide in liquid ammonia followed by the addition of finely divided sodium or lithium metal until the blue color persists, and reacting the thus obtained tri-metal salt with the 5-p-toluenesulfonyl-, 5-bromo- or 5-chloro- derivative of 2',3'-isopropylidene adenosine having the structure

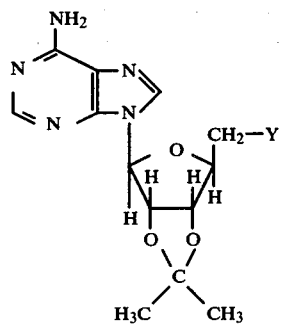

wherein Y is p-toluenesulfonyl, chlorine or bromine for about two hours in liquid ammonia followed by acid hydrolysis and treatment with methyl iodide in acidic solvents, such as formic acid, acetic acid or mono-, di- and trichloroacetic acids.

The compounds of this invention wherein $R_1$ is a straight or branched alkoxy group of from 1 to 8 carbon atoms are prepared from the corresponding derivatives wherein $R_1$ is hydroxy by reaction with an alcohol of the formula $R_8OH$, wherein $R_8$ is a straight or branched alkyl group of from 1 to 8 carbon atoms, saturated with HCl gas at about 25° C. for about 12 to 36 hours.

The compounds of general Formula I wherein $R_1$ is a straight or branched alkoxy group of from 1 to 8 carbon atoms may also be prepared by converting the corresponding compound wherein $R_1$ is hydroxy to the acid halide by, for example, treatment with thionyl chloride, followed by alcoholysis with an alcohol of the formula $R_8OH$ as defined above by procedures generally known in the art.

The compounds of this invention wherein $R_1$ is $-NR_4R_5$ wherein each of $R_4$ and $R_5$ is hydrogen or a lower alkyl group of from 1 to 4 carbon atoms are prepared by an acylation reaction of an acid halide, for example, an acid chloride, of the corresponding compound wherein $R_1$ is hydroxy and R has the meaning defined in Formula I with the proviso that any free amino group is suitably protected with, for example, carbobenzyloxy or tert-butoxycarbonyl, with an excess of an appropriate amine which may be represented as $HNR_4R_5$. The reaction is carried out in methylene chloride, chloroform, dimethyl formamide, or ethers such as tetrahydrofuran and dioxane, or benzene at about 25° C. for about 1 to 4 hours. Suitable amines are ammonia, or a compound which is a potential source of ammonia, for example, hexamethylenetetramine; primary amines, for example, methylamine, ethylamine or n-propylamine; and secondary amines, for example, dimethylamine, diethylamine or di-n-butylamine. Following the acylation reaction the α-amine protecting groups are removed by treatment with acid, for example, trifluoroacetic acid or hydrogen bromide in dioxane.

The compounds of general Formula I wherein $R_1$ is

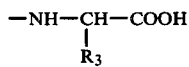

are prepared by reacting the corresponding derivative wherein $R_1$ is hydroxy or a functional derivative thereof such as an acid anhydride and R has the meaning defined in Formula I with the proviso that any free amino group is protected with a suitable blocking group, such as benzyloxycarbonyl or tert-butoxycarbonyl with a compound of the structure

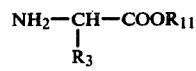

wherein $R_3$ has the meaning defined in general Formula I and $R_{11}$ is a lower alkyl group, for example, methyl or ethyl in an ether solution, such as, tetrahydrofuran or dioxane at about 0° C. to 50° C. for about 1 to 24 hours followed by acid hydrolysis, for example, with trifluoroacetic acid or hydrogen bromide in dioxane for about 1 to 20 hours to remove the protecting group(s), with the proviso that when the amine protected free acid is employed the reaction is carried out using a dehydrating agent such as dicyclohexylcarbodiimide.

The compounds of general Formula I wherein R is alkylcarbonyl wherein the alkyl moiety is straight or branched and has from 1 to 4 carbon atoms and $R_1$ is hydroxy are prepared by treating the corresponding derivative wherein R is hydrogen with an acid halide of the formula

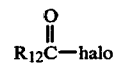

wherein halo is a halogen atom, for example, chlorine or bromine and $R_{12}$ is a straight or branched alkyl group having from 1 to 4 carbon atoms or an appropriate acid anhydride, in water in the presence of a base such as sodium hydroxide or sodium borate at a temperature of about 0° to 25° C. for about ½ hour to 6 hours. These compounds may also be prepared from the ester derivative, that is, compounds of general Formula I wherein R is hydrogen and $R_1$ is an alkoxy group of from 1 to 8 carbon atoms by treatment with the acid halide,

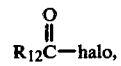

described above, in water, methylene chloride, chloroform or dimethyl acetamide in the presence of a base such as sodium hydroxide, potassium hydroxide or excess triethylamine at a temperature of about 0° to 25° C. for about ½ hour to 24 hours.

The compounds of general Formula I wherein R is alkoxycarbonyl wherein the alkoxy moiety is straight or branched and has from 1 to 4 carbon atoms are prepared by treating the corresponding derivative wherein R is hydrogen and $R_1$ is hydroxy with a halo alkylformate of the formula

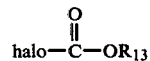

wherein halo is a halogen atom such as chlorine or bromine and $R_{13}$ is a straight or branched alkyl group having from 1 to 4 carbon atoms in water in the presence of a base such as sodium hydroxide or sodium borate at a temperature of about 0° to 25° C. for about ½ hour to 6 hours.

The compounds of general Formula I wherein R is

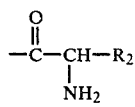

wherein $R_2$ is hydrogen, a straight or branched lower alkyl group of from 1 to 4 carbon atoms, benzyl or p-hydroxybenzyl are prepared by treating the corresponding derivative wherein R is hydrogen and $R_1$ is a straight or branched alkoxy group of from 1 to 8 carbon atoms with an acid of the formula

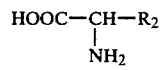

or an anhydride thereof wherein the amino group is protected with a suitable blocking group such as benzyloxycarbonyl or tert-butoxycarbonyl and $R_2$ has the meaning defined hereinabove in an ether, such as, tetrahydrofuran or dioxane, methylene chloride or chloroform and in the presence of a dehydrating agent, such as, dicyclohexylcarbodiimide when the free acid is employed, at a temperature of about 0° to 35° C. for about 1 to 12 hours followed by acid hydrolysis using trifluoroacetic acid or HBr/dioxane and base hydrolysis to remove the protecting groups.

The individual optical isomers of compounds of Formula I wherein R is hydrogen and $R_1$ is hydroxy may be resolved using a (+) or (−) binaphthylphosphoric acid salt by the method of R. Viterbo et al., Tetrahedron Letters 48, 4617 (1971). Other resolving agents such as (+) camphor-10-sulfonic acid may also be employed. When Z is $RHN(CH_2)_n$—and R is hydrogen resolution is achieved using the lactam of said compounds. The individual optical isomers of compounds wherein R and $R_1$ are other than hydrogen or hydroxy may be obtained as described herein for the racemic mixture only starting with the resolved amino acid.

The lactams of this invention, that is, compounds of general Formula II are prepared by heating an ester of the corresponding amino acid of the structure

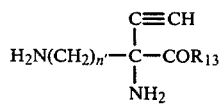

Compound 7 wherein $R_{13}$ is a straight or branched alkoxy group of from 1 to 8 carbon atoms, and n′ is the integer 3 or 4 in a lower alcohol such as 2-methoxyethanol or ethanol for about 1 to 24 hours at a temperature of about 80° to 120° C. The lactams may also be prepared by treating the free amino acid derivative with a dehydrating agent, such as, cyclohexylcarbodiimide.

The compounds of general Formula V wherein R is hydrogen are prepared by coupling 7-aminocephalosporanic acid or a derivative thereof having the formula

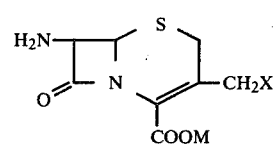

Formula VI wherein M is hydrogen or a negative charge and X is hydrogen or acetoxy, with an acid of the formula

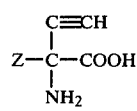

Formula VII or a functional derivative thereof, such as, the acid chloride or an acid anhydride in the presence of a dehydrating agent such as dicyclohexylcarbodiimide wherein Z has the meaning defined in general Formula I and the amino group is protected with a suitable blocking group, for example, tert-butoxycarbonyl followed by acid hydrolysis to remove the amino protecting groups.

The coupling reaction is generally carried out in a solvent, such as, ethyl acetate, dioxane, chloroform or tetrahydrofuran in the presence of a base, such as, alkaline bicarbonate. The temperature of the reaction may vary from about −10° C. to 100° C., and the reactive time may vary from about ½ hour to 10 hours. The cephalosporin products are isolated by conventional procedures. The compounds of Formula VII are prepared by procedures described hereinabove, and the compounds of Formula VI are commercially available.

The compounds of Formula V wherein R is other than hydrogen are prepared from the corresponding derivatives wherein R is hydrogen by the general procedures set forth hereinabove for compounds of general Formula I wherein R is other than hydrogen The following Example 1 illustrates the use of a compound of general Formula I wherein $R_1$ is hydroxy as a chemical intermediate in the preparation of a cephalosporin of Formula V.

EXAMPLE 1

7-[[2-Acetylene-2,5-diaminovaleryl]amino]-3-acetyloxymethyl-8-oxo-5-thia-1-azabicyclo[4.2.0]oct-2-ene-2-carboxylic acid A mixture of 1 g of 3-acetyloxy-7-amino-8-oxo-5-thia-1-azabicyclo[4.2.0]oct-2-ene-2-carboxylic acid and 1 g of 2-acetylene-2,5-diaminovaleric acid chloride wherein the free amino groups are protected with tert-butoxycarbonyl in 50 ml of ethylacetate is refluxed for 2 hours after which the solvent is removed leaving a residue which is treated with mild acid and chromatographed on silica gel using benzene-acetone as the eluant to give 7-[[2-acetylene-2,5-diaminovaleryl]amino]-3-acetyloxymethyl-8-oxo-5-thia-1-azabicyclo[4.2.0]oct-2-ene-2-carboxylic acid.

EXAMPLE 2

An illustrative composition for hard gelatin capsules is as follows:

| | | |
|---|---|---|
| (a) | α-acetylene-α,δ-diaminovaleric acid | 20 mg |
| (b) | talc | 5 mg |

| | | |
|---|---|---|
| (c) | lactose | 90 mg |

The formulation is prepared by passing the dry powders of (a) and (b) through a fine mesh screen and mixing them well. The powder is then filled into hard gelatin capsules at a net fill of 115 mg per capsule.

EXAMPLE 3

An illustrative composition for tablets is as follows:

| | | |
|---|---|---|
| (a) | α-acetylene-α-amino-δ-guanidino-valeric acid | 20 mg |
| (b) | starch | 43 mg |
| (c) | lactose | 45 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 4

An illustrative composition for an injectable suspension is the following 1 ml ampul for an intramuscular injection.

| | | Weight per cent |
|---|---|---|
| (a) | α-acetylene-α-amino-γ-methyl-thiobutyric acid | 1.0 |
| (b) | polyvinylpyrrolidone | 0.5 |
| (c) | lecithin | 0.25 |
| (d) | water for injection to make | 100.0 |

The materials (a)-(d) are mixed, homogenized, and filled into 1 ml ampuls which are sealed and autoclaved 20 minutes at 121° C. Each ampul contains 10 mg per ml of novel compound (a).

The following examples further illustrate the compounds of the invention.

EXAMPLE 5

α-Acetylene-α,δ-diaminovaleric acid 11.8 g (0.048 M) of N-(3-trimethylsilylprop-2-ynyl)-benzenecarboximidate in 20 ml of tetrahydrofuran is added to lithium diisopropylamide, prepared from 4.9 g (6.78 ml, 0.048 M) of diisopropylamide in 60 ml of tetrahydrofuran and 23.6 ml of a 2.05 M solution of n-butyllithium at −70° C. after which 9.5 g (0.042 M) of N-(3-bromopropyl)benzylimine is added, and the mixture is stirred at −70° C. for 5½ hours. To the reaction mixture is added 23.6 ml of a 2.05 M solution of n-butyllithium followed by the addition of 4.5 g (3.67 ml, 0.048 M) of methyl chloroformate. After 30 minutes at −78° C. the mixture is treated with brine, and the reaction product is isolated by ether extraction. The ether extract is evaporated and 300 ml of 3 N HCl is added to the resulting residue and the mixture is refluxed for 7 hours. On cooling the mixture is washed well with methylene chloride, made alkaline and washed again. The aqueous solution is acidified and concentrated to dryness. The residue is triturated with ethanol, filtered and the ethanol evaporated. The residue is dissolved in water, the pH adjusted to 6, and the solution is applied to a column of Amberlite 120 H+, eluting with 1 M NH4OH which affords, upon recrystallization from ethanol-water, α-acetylene-α,δ-diaminovaleric acid, M.P. 168–169 (dec.).

In the above procedure N-(3-bromopropyl)benzylimine is prepared from 3-bromopropylamine and benzaldehyde by procedures generally known in the art.

EXAMPLE 6

α-Acetylene-α,ε-diaminocaproic acid

When in the procedure of Example 5 an appropriate amount of N-(4-bromobutyl)benzylimine, prepared from 4-bromobutylamine and benzaldehyde by procedures generally known in the art, is substituted for N-(3-bromopropyl)benzylimine, α-acetylene-α,ε-diaminocaproic acid is obtained.

EXAMPLE 7

α-Acetylene-α-amino-γ-benzylthiobutyric acid

A solution of 21.5 g (0.1 M) of 3-trimethylsilylprop-2-ynyl-1-iminobenzyl in 400 ml of tetrahydrofuran at −78° C. is treated with n-butyllithium (50 ml of a 2.0 M solution) afterwhich 18.6 g (0.1 M) of S-benzyl-2-chloroethanthiol in 20 ml of tetrahydrofuran is added and the solution is maintained at −30° C. for 15 hours. The solution is cooled to −78° C. and treated with n-butyllithium (50 ml of a 2.0 M solution) followed by the addition of 9.4 g (0.1 M) of methylchloroformate. After 15 minutes at −78° C. the mixture is treated with brine, extracted with ether and the ether extract evaporated leaving a residue which is treated with 400 ml of a 2 M solution of aqueous hydrochloric acid and refluxed for 12 hours. The aqueous solution is extracted with methylene chloride, made alkaline and reextracted. The aqueous solution is then made acidic and evaporated to dryness leaving a residue. The residue is triturated with ethanol, filtered and the filtrate evaporated. The residue is dissolved in water, the pH adjusted to 6 and the solution is applied to an Amberlite (120 H+) resin, eluting with 2M NH4OH which affords, upon recrystallization from ethanol-water, α-acetylene-α-amino-γ-benzylthiobutyric acid.

EXAMPLE 8

α-Acetylene-α-amino-γ-methylthiobutyric acid

When in the procedure of Example 7 an appropriate amount of S-methyl-2-chloroethanthiol is substituted for S-benzyl-2-chloroethanthiol, α-acetylene-α-amino-γ-methylthiobutyric acid is obtained.

EXAMPLE 9

α-Acetylene-α-amino-γ-[S-(5'-desoxyadenosin-5'-yl)-S-(methyl)thio]butyric acid

To 20 mM of sodium amide in 200 ml of ammonia is added 10 mM of α-acetylene-α-amino-γ-benzylthiobutyric acid, prepared in Example 7. After 1 hour sodium metal in small pieces is added until the blue color persists for 5 minutes then 10 mM of 2',3'-isopropylidene-5'-p-toluenesulfonyl adenosine is added. The ammonia is allowed to evaporate. The residue is treated with 1 N H2SO4 for 48 hours at 25° C., then the pH is adjusted to 6 and the solution applied to an ion exchange resin KV-2NH4+ and then a DEAE cellulose (OH−) column. The aqueous eluate is evaporated and the residue recrystallized from water/ethanol to give 5'-deoxy-5'-(3-amino-3-carboxypent-4-ynylthio)-adenosine, which is dissolved in a mixture of acetic acid (4 ml) and formic acid (4 ml). Methyl iodide (1 ml) is added and the mixture kept under N₂ for 6 days at 25° C. The solvents are removed under reduced pressure at 25° C. and the residue dissolved in 0.1 N HCl (8 ml). A saturated solution of Reinecke salt is added and the resultant precipitate collected and treated with silver sulfate (1.5 g) in acetone at 25° C. for 36 hours. The insoluble residue is filtered off and washed with methanol. The combined filtrates are concentrated under reduced pressure to yield α-acetylene-α-amino-γ-[S-(5'-desoxyadenosin-5'-yl)-S-(methyl)thiol]- butyric acid.

EXAMPLE 10

α-Acetylene-α-amino-δ-quanidinovaleric acid

To a solution of 3.9 g (0.025 M) of α-acetylene-α,δ-diaminovaleric acid monohydrochloride, prepared from the compound of example 5 by treatment with hydrochloric acid, in 10 ml of a 2 M solution of sodium hydroxide is added 9.25 g (0.05 M) of ethylthiouronium hydrobromide. The pH of the solution is adjusted to 10 by the addition of about 15 ml of a 2 M solution of sodium hydroxide and so maintained for 48 hours during which time the solution is stirred at room temperature. The residue obtained after neutralization with concentrated hydrochloric acid and evaporation of the solvent is passed through a column of Amberlite 120 H+ eluting with a 2 M solution of ammonia. The fractions giving a positive ninhydrin are collected and concentrated to yield a white residue which is crystallized from water-ethanol to give α-acetylene-α-amino-δ-guanidinovaleric acid.

EXAMPLE 11

Methyl-2-acetylene-2,5,-diaminovalerate dihydrochloride

2-Acetylene-2,5-diaminovaleric acid (500 mg, 3.2 mM) is added to methanol (40 ml) which had been saturated with dry hydrogen chloride. The solution is heated at reflux for 12 hours, then the solvent is evaporated to afford methyl-2-acetylene-2,5,-diaminovalerate dihydrochloride.

EXAMPLE 12

2-Acetylene-2,5-di-(1-oxoethylamino)valeric acid

To a solution of 312 mg (2.0 mM) of 2-acetylene-2,5-diamino valeric acid in 2.5 ml of 1 N sodium hydroxide at 0° C. are added simultaneously from two syringes 312 mg (4 mM) of acetyl chloride diluted in 1 ml of THF and 4 ml of 1 N sodium hydroxide. After 30 minutes at 0° C. the solution is acidified by the addition of 6 N hydrochloric acid, then extracted well with dichloromethane. The organic phase is dried and concentrated to afford 2-acetylene-2,5-di-(1-oxoethylamino)valeric acid.

In a similar manner only substituting an appropriate amount of ethyl chloroformate for acetyl chloride, 2-acetylene-2,5-di-(1-ethoxycarbonylamino)valeric acid is obtained.

EXAMPLE 13

2-Acetylene-2,5-di-N-(2-aminopropylcarbonyl)valeric acid

A solution of 240 mg (1 mM) of methyl-2-acetylene-2,5-diaminovalerate dihydrochloride in 4 ml of methylene chloride containing 200 mg of triethylamine is treated with 440 mg (2 mM) of N-carbobenzoxy alanine and 412 mg (2 mM) of N,N'-dicyclohexylcarbodiimide overnight at 25° C. The mixture is then cooled to 0° C. and the precipitated dicyclohexyl urea filtered off. The filtrate is diluted with methylene chloride, washed with water, bicarbonate, dilute hydrochloric acid, then dried and concentrated. The residue is treated with 10 ml of ethanol and 10 ml of a 40% (w/w) solution of hydrogen bromide in dioxane for 30 minutes at 25° C. after which 50 ml of ether is added and the resulting precipitate collected. The precipitate is treated with 15 ml of 1 N aqueous sodium hydroxide overnight at 25° C. The pH of the solution is adjusted to neutral and the product isolated from an Amberlite 120 H+ resin by elution with 2 M ammonium hydroxide to give 2-acetylene-2,5-di-N-(2-aminopropylcarbonyl)valeric acid.

EXAMPLE 14

N-Propyl-2-acetylene-2,5-diamino valeramide dihydrobromide

To a solution of 312 mg (2 mM) of 2-acetylene-2,5-diaminovaleric acid in 2.5 ml of 1 N aqueous sodium hydroxide at 0° C. are added simultaneously from two syringes 680 mg (4 mM) of benzyl chloroformate in dioxane (2 ml) and 4 ml of 1 N sodium hydroxide. After 30 minutes at 0° C. the solution is acidified by the addition of 6 N hydrochloric acid, then extracted well with dichloromethane. The organic phase is dried and concentrated to afford 2-acetylene-2,5-di-(benzyloxycarbonylamino)valeric acid which is dissolved in 15 ml of dichloromethane and treated with 220 mg of thionyl chloride at 25° C. for one hour. Propylamine (250 mg) is then added and the solution stirred at 25° C. for one hour, then washed with water, dried and concentrated. The residue is treated with 12 ml of a solution of dioxane containing hydrogen bromide (40% w/w) and allowed to stand for 30 minutes at 25° C. Ether (50 ml) is then added and the resulting precipitate collected to afford N-propyl-2-acetylene-2,5-diamino valeramide dihydrobromide.

EXAMPLE 15

2-(2-Acetylene-2,5-diamino-1-oxopentylamino)propionic acid

To 424 mg (1 mM) of 2-acetylene-2,5-di-(benzyloxycarbonylamino)valeric acid in 15 ml of methylene chloride is added 205 mg (2 mM) of triethylamine followed by 109 mg (1 mM) of ethyl chloroformate. The solution is stirred for one hour at 25° C., then 103 mg (1 mM) of alanine methyl ester in 5 ml of methylene chloride is added. This solution is kept overnight at 25° C., washed with water, dried and evaporated to dryness. The residue is treated with 10 ml of a 40% (w/w) solution of hydrogen bromide in dioxane at 25° C. for 30 minutes. Ether (50 ml) is then added and the precipitate collected. The precipitate is treated with 40 ml of a 1 N sodium hydroxide solution overnight at 25° C., the pH adjusted to 6.5, and applied to an Amberlite 120 H+ resin. Elution with 2 N ammonium hydroxide affords 1-(2-acetylene-2,5-diamino-1-oxopentylamino)propionic acid.

EXAMPLE 16

3-Amino-3-acetylene-2-piperidone

Sodium (0.46 g) is added to methoxyethanol (30 ml) under nitrogen. After the sodium has dissolved, 2.5 g of methyl-2-acetylene-2,5-diaminovalerate dihydrochloride in 10 ml of methoxyethanol is added and the solution heated at reflux for 3 hours. The solvent is then evaporated under reduced pressure and the residue extracted with ether. The ether solution is evaporated to yield a residue which is recrystallized from chloroform pentane to give 3-amino-3-acetylene-2-piperidone.

EXAMPLE 17

Methyl-2-acetylene-2,5-di-(1-oxoethylamino)valerate

A solution of 170 mg (1 mM) of 2-acetylene-2,5-di-(1-oxoethylamino)valeric acid in 10 ml of chloroform is cooled to −5° C. and 78 mg of thionyl chloride in chloroform is added. After 30 minutes 1 ml of methanol is added. Evaporation of the solvent yields methyl-2-acetylene-2,5-di-(1-oxoethylamino)valerate.

We claim:

1. A compound of the formula

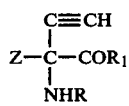

wherein Z is β-methylthioethyl, β-benzylthioethyl, S-(5′-desoxyadenosin-5′-yl)-S-methylthioethyl, γ-guanidinopropyl, or $RHN(CH_2)_n-$; n is the integer 3 or 4; each R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or the group

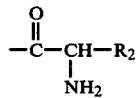

wherein $R_2$ is hydrogen, a straight or branched lower alkyl group of from 1 to 4 carbon atoms, benzyl or p-hydroxybenzyl; and $R_1$ is hydroxy, a straight or branched alkoxy group of from 1 to 8 carbon atoms, $-NR_4R_5$ wherein each $R_4$ and $R_5$ is hydrogen or a lower alkyl group of from 1 to 4 carbon atoms, or the group

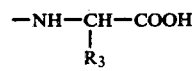

wherein $R_3$ is hydrogen, a straight or branched lower alkyl group of from 1 to 4 carbon atoms, benzyl or p-hydroxybenzyl; with the provisos that when Z is β-benzylthioethyl or S-(5′-desoxyadenosin-5′-yl)-S-methylthioethyl, R is hydrogen and $R_1$ is hydroxy, when Z is γ-guanidinopropyl, R is hydrogen and $R_1$ is hydroxy or a straight or branched lower alkoxy group of from 1 to 8 carbon atoms, and when Z is $RHN(CH_2)_n-$both R groups are the same; and the lactams thereof when Z is $RHN(CH_2)_n-$and R is hydrogen; and pharmaceutically acceptable salts and individual optical isomers thereof.

2. A compound of claim 1 wherein $R_1$ is hydroxy.

3. A compound of claim 2 wherein Z is β-methylthioethyl, S-(5′-desoxyadenosin-5′-yl)-S-methylthioethyl, γ-guanidinopropyl or $RHN(CH_2)_n-$.

4. A compound of claim 1 wherein each R is hydrogen.

5. A compound of claim 1 wherein Z is $RHN(CH_2)_n-$.

6. A compound of claim 5 which is α-acetylene-α,δ-diaminovaleric acid.

7. A compound of claim 1 of the formula:

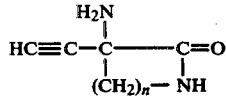

wherein n is 3 or 4.

8. A compound of claim 7 wherein n is 3.

* * * * *